United States Patent
Avudainayagam et al.

(10) Patent No.: US 7,289,254 B2
(45) Date of Patent: Oct. 30, 2007

(54) OPTOMETRY MEASUREMENT DEVICE

(75) Inventors: Kodikullam V Avudainayagam, Amcliffe NSW (AU); Chitralekha S Avudainayagam, Amcliffe NSW (AU)

(73) Assignee: Queensland University of Technology, Brisbane (AU)

( * ) Notice: Subject to any disclaimer, the term of this patent is extended or adjusted under 35 U.S.C. 154(b) by 400 days.

(21) Appl. No.: 10/967,593

(22) Filed: Oct. 18, 2004

(65) Prior Publication Data

US 2005/0052715 A1  Mar. 10, 2005

Related U.S. Application Data

(63) Continuation of application No. PCT/AU03/00487, filed on Apr. 24, 2003.

(30) Foreign Application Priority Data

Apr. 26, 2002 (AU) .................... PS1968

(51) Int. Cl.
*G02B 5/32* (2006.01)

(52) U.S. Cl. .................. 359/15; 351/237; 351/240

(58) Field of Classification Search .................. 359/1, 359/15; 351/239–246, 237
See application file for complete search history.

(56) References Cited

FOREIGN PATENT DOCUMENTS

| DE | 3405778 | * | 8/1985 |
|----|---------|---|--------|
| DE | 3405778 A1 | | 8/1985 |
| JP | 09166955 A2 | | 6/1997 |
| WO | WO 92/201417 | | 2/1992 |
| WO | WO 02/011612 A1 | | 2/2002 |

* cited by examiner

*Primary Examiner*—Leonidas Boutsikaris

(57) ABSTRACT

The present invention features a method and device for measuring characteristics of the human eye, particularly spherical refractive error. The device comprises a recorded hologram of an array of elements each bearing an identifying indicia. When the reconstructed hologram is viewed by a subject each of the indicia appear at different virtual distances. By indicating which indicia appear to be in focus the spherical refractive error of the eye and the range of accommodation is determined. The indicia are conveniently numbers that indicate dioptres. Also described is an apparatus for working the method. The apparatus can also be used to determine cylinder power and axis, binocular refraction and stereopsis.

16 Claims, 4 Drawing Sheets

OPTOMETRY MEASUREMENT DEVICE

CROSS-REFERENCE TO RELATED APPLICATIONS

This application is a continuation of International Patent Application No. PCT/AU03/00487, filed Apr. 24, 2003, which claims priority to Australian Patent Application No. PS 1968, filed Apr. 26, 2002, each of which is hereby incorporated by reference in its entirety.

The invention relates to a method and apparatus for determining spherical refractive error and the amplitude (range) of accommodation of the human eye simultaneously. The method and apparatus may be extended to estimate the cylinder power and axis, test binocular vision, and test stereopsis.

BACKGROUND TO THE INVENTION

The primary method for determining spherical refractive error of the human eye is to sequentially display targets to a patient and seek his/her responses to identify which object appears to be sharpest. A determination of the myopia (short-sightedness) or hypermetropia (long-sightedness) of the patient is made. The method is well established and has been used by optometrists for many years as the basis for determining the correct prescription for glasses and contact lenses.

The spherical refractive power (power of the lens required to correct ametropia) for the vast majority of people is between −5 dioptres and +2.5 dioptres. The accommodation range of a person (the range through which the refractive power of the eye can be varied) depends on his/her age and reduces with increasing age. Typically, the amplitude of accommodation of a 10 yr. old child is of the order of 10 to 14 dioptres, of a 20 yr. old around 9 to 12 dioptres, for a 40 yr. old it falls to between 4 and 6 dioptres, and for a 60 yr. old it falls to a value of less than or about a dioptre.

Notwithstanding the ubiquitous acceptance of the current method, a simultaneous presentation of targets with different vergences to the subject's eye would enormously simplify the measurement procedure for both the optometrists as well as the subject. It would also be valuable if a measure of the amplitude of accommodation is obtained at the same time. A simple and quick procedure to estimate the cylinder power and axis of the eye would be rewarding. It would be advantageous to have multiple vergence targets for each eye to conduct binocular refraction especially for spherical balancing. It is also highly desirable to have a truly three-dimensional target for testing stereopsis.

Various optical techniques for measuring characteristics of the human eye have been developed with advances in optical technology. One interesting approach is described in German patent application number 19514656 in the name of Occulus Optikgeraete GMBH. The described invention records a reflection hologram of the cornea of the eye which is then digitised for analysis.

Other approaches, such as that described in International publication number WO2002011612 in the name of Tracey Technologies LLC, use a light source to probe the eye. Reflections from the retina are analysed to determine aberration refraction.

Some techniques use multiple measurements and computer analysis to determine optimal corneal shaping for precise vision. Reference may be had to International publication WO199201417 in the name of Larry Horwitz for a description of this technology.

The prior art mentioned above is representative of the various optical techniques that have been applied to vision analysis and correction. They are universally complex and generally invasive. A much simpler and non-invasive approach is needed.

OBJECT OF THE INVENTION

It is an object of the present invention to provide an inexpensive, portable device as well as a quick and easy method for measuring the spherical refractive error of the human eye subjectively.

It is another object to provide a simple method and device for measuring the amplitude of accommodation.

It is a further object to provide an easy method to estimate the cylinder power and axis of the human eye.

It is also an object to provide a device for binocular refraction and spherical balancing.

It is a yet further object to provide an arrangement to test stereopsis.

Further objects will be evident from the following description.

DISCLOSURE OF THE INVENTION

In one form, although it need not be the only or indeed the broadest form, the invention resides in a device for measuring spherical refractive error of the human eye of a subject comprising:

an holographic element recording an image wavefront of a three dimensional array of indicia; and means for illuminating the holographic element with a plane wavefront of visible light such that when viewed the patient sees a reconstructed image of the array of indicia;

wherein each indicia is seen at a different perceived distance from the subject.

Suitably the array of indicia comprises a 4 by 4 array with labels ranging from −10 through zero to +5.

In a further form, the invention resides in a method of measuring spherical refractive error of the human eye of a patient including the steps of:

the subject viewing a holographic reconstructed array of elements with each element at a different perceived distance from the subject, and each said element bearing indicia; and the subject identifying one or more indicia that are seen to be in sharp focus.

Suitably the method includes the further step of the subject identifying the range of indicia that are in focus to give a measure of his/her amplitude of accommodation.

In another form of the invention the array of indicia comprises radial line patterns. The angular separation between the adjacent lines of the radial pattern is set to be about 10°. The invention resides further in a method of estimating the cylinder axis and power of the eye which includes a step in which the subject views the hologram that is suitably illuminated and identifies the two indicia for which sharpest lines are seen. From the subject's response his/her cylinder power and axis are estimated.

The invention in a further form resides in presenting two holograms one to each eye to facilitate spherical balancing binocularly.

In a still further form, the invention resides in an apparatus for testing the stereopsis of a patient and comprises a large hologram recording a suitable three-dimensional scene. The hologram is made large enough so that it can be viewed by both the eyes simultaneously to enable testing of stereopsis.

BRIEF DETAILS OF THE DRAWINGS

To assist in understanding the invention preferred embodiments will now be described with reference to the following figures in which.

DETAILED DESCRIPTION OF THE DRAWINGS

Figure 1:
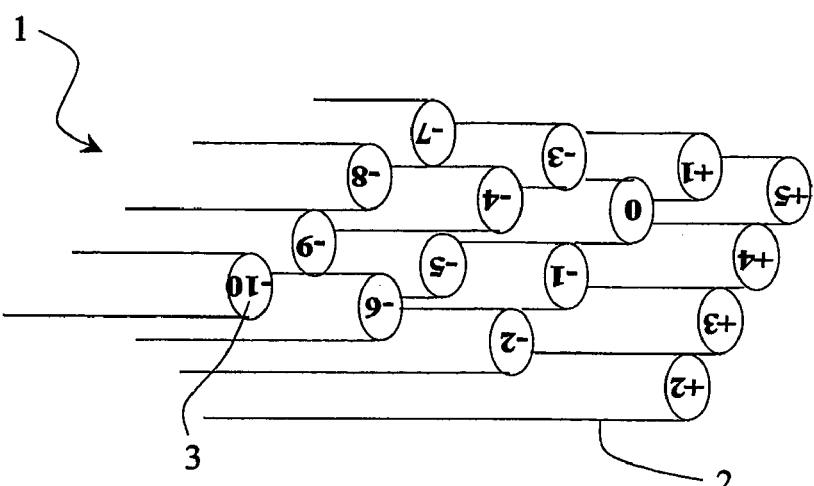
FIG. 1 shows a special 3D object used for recording the hologram.

In describing different embodiments of the present invention common reference numerals are used to describe like features.

Referring to FIG. 1 there is shown one embodiment of a three dimensional target 1 suitable for working the invention. The target is formed from a 4×4 array of pegs 2 each having indicia 3 at one end. Each indicia is positioned at a different distance in space with respect to a lens that is used to record a hologram of the target, as described below.

One of the pegs is labeled zero in the preferred embodiment shown in FIG. 1. The remaining pegs are labeled with different indicia. The inventors have found that it is convenient for the remaining pegs to be labeled with numbers that can indicate spherical refractive power required for correction. The nearest adjacent pegs to the zero pegs are labeled −1 and +1, the next nearest −2 and +2, etc. The relative distances between the pegs can be obtained from the object distances 'u' given in Table 1 below.

Figure 2:
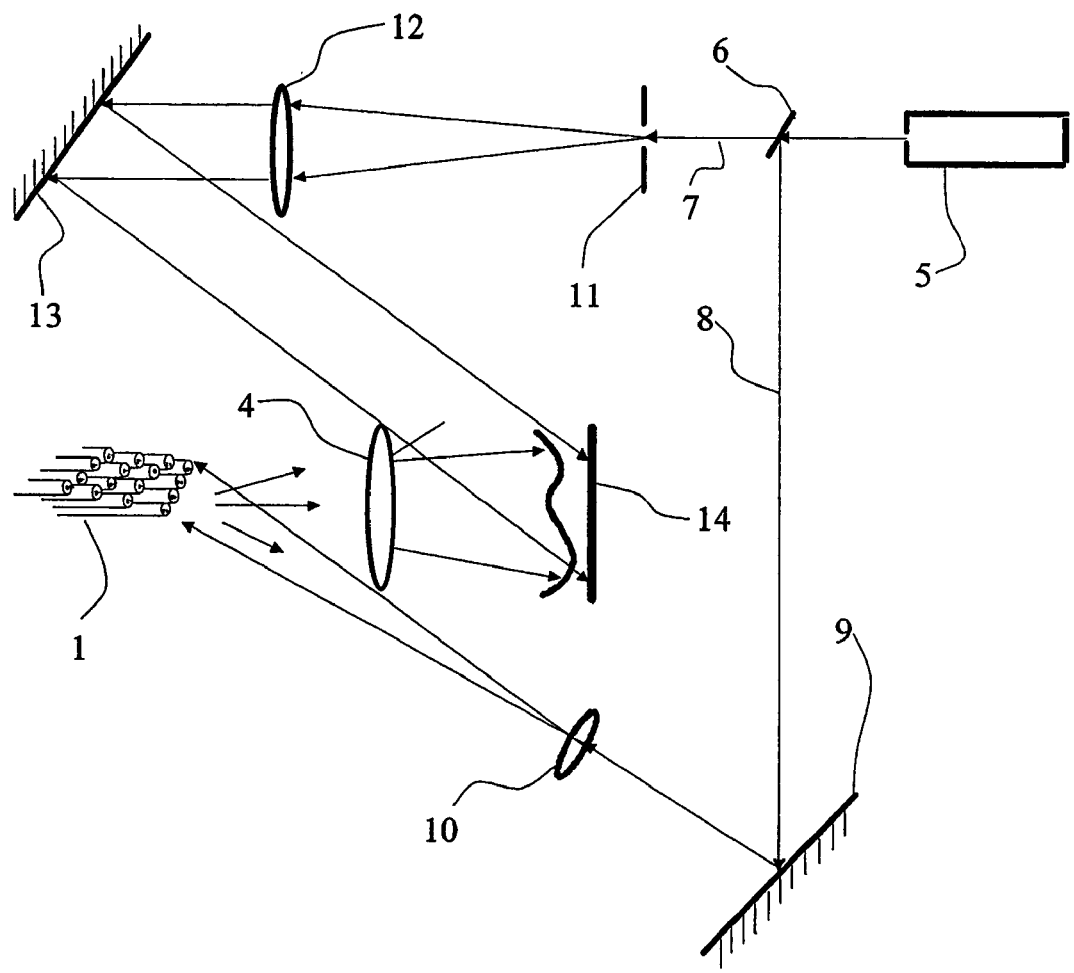
FIG. 2 shows a recording geometry.

The arrangement for recording a hologram of the target is shown in FIG. 2. The recording arrangement is a conventional arrangement for recording a hologram of a three dimensional object. The target 1 is positioned with the zero peg positioned at the focus of a 20D lens 4. A beam from helium neon laser 5 is split by beamsplitter 6 to form a reference beam 7 and an object beam 8. The object beam 8 is directed via mirror 9 and through divergent lens 10 (f=1.2 cm) to paint the object 1 with coherent radiation. The reference beam 7 passes through a spatial filter 11 to ensure a single spatial mode beam is used. A collimating lens 12 collects the beam which is redirected by mirror 13 to holographic recording medium 14. Scattered radiation from the object 1 is collected by the 20D lens 4 and directed to the holographic recording medium 14. Care is taken to ensure that the reference beam and the object beam path lengths are matched at the recording plane. The interference between the scattered object beam and the reference beam is recorded on the holographic recording medium 14, such as holographic plate (Slavich PFG-01M or 8E75 Agfa or equivalent).

Agfa 8E75 plates require ≈50 μJ/cm² for 50% transmission. The exposure time in the example was about 1 hr as a low power laser (~1 mw) was used. The reference beam intensity was adjusted visually to be a little greater than the object beam intensity to obtain good fringe contrast. The recorded hologram was developed for 6 min in Kodak D19 developer and bleached for 4 min in a reversal bleach (Sodium Hydrogen Sulphate 80 g, Potassium Dichromate 5 g, in 1 litre of water) to obtain a phase hologram.

The following table shows object distances, u, and labels corresponding to image vergences of +5.0D to −2.5D for a 20D lens in the arrangement described above.

TABLE 1

| Printed number (object label) | u (in cm) | image vergence (in dioptre) |
| --- | --- | --- |
| +5 | 4.444 | −2.5 |
| +4 | 4.545 | −2.0 |
| +3 | 4.651 | −1.5 |
| +2 | 4.762 | −1.0 |
| +1 | 4.878 | −0.5 |
| 0 | 5.000 | 0.0 |
| −1 | 5.128 | 0.5 |
| −2 | 5.263 | 1.0 |
| −3 | 5.405 | 1.5 |
| −4 | 5.556 | 2.0 |
| −5 | 5.714 | 2.5 |
| −6 | 5.882 | 3.0 |
| −7 | 6.061 | 3.5 |
| −8 | 6.250 | 4.0 |
| −9 | 6.452 | 4.5 |
| −10 | 6.667 | 5.0 |

Figure 3:
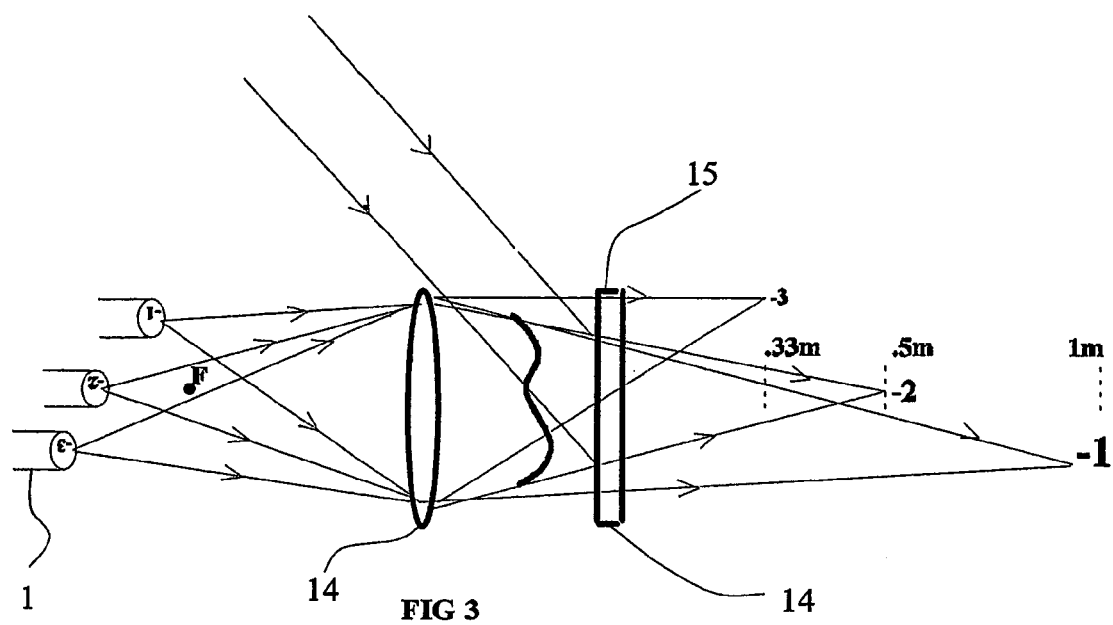
FIG. 3 shows an enlarged section of the recording geometry with a sample object.

An enlarged view of the recording geometry is shown in FIG. 3, which indicates the perceived distances of the object recorded by the 20D lens. For example, the pegs labeled −1, −2 and −3 are positioned at 5.128 cm, 5.263 cm and 5.405 cm respectively. Each peg is recorded with a virtual depth of 0.33 m, 0.5 m and 1 m respectively. When the recorded hologram is illuminated by the reference beam at the same angle as was used to record it (see FIG. 3) the recorded object wavefront 15 is recreated to form the images at these distances.

Figure 4:
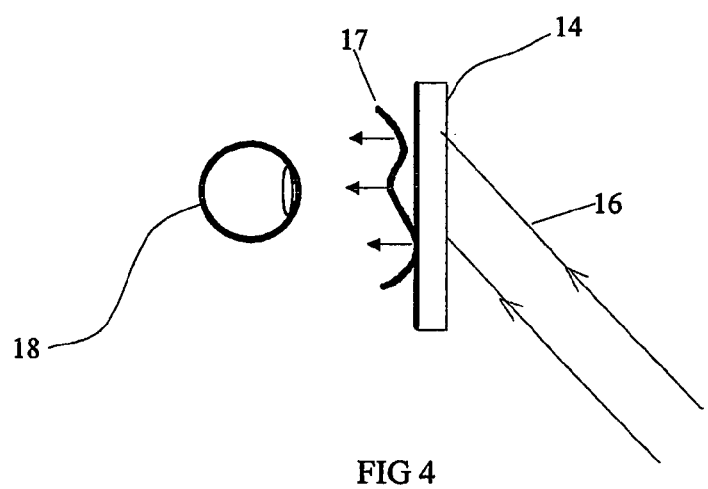
FIG. 4 shows a reconstruction geometry.

However, to work the invention, the hologram is illuminated by a reverse reference beam 16 traveling in the opposite direction, as shown in FIG. 4, to generate the phase conjugate of the recorded object wavefront 17. The eye 18 is located roughly at the position of the 20D lens 4 to view the hologram. The subject therefore sees the images as if they were formed in space by the forward traveling object wavefront that was recorded. The character size on the labels is chosen to correspond to a visual acuity of around 20/200 in the image. The image of the entire array occupies ±5°. The eye has to rotate very slightly to view the various targets, which is automatically done by the subject. The label size can be reduced to 20/100 visual acuity to reduce the field of view to half the size if required.

The images seen clearly by the patient are those that fall within his/her accommodation range. The highest number (algebraically) seen by the subject corresponds to the spherical refraction error as this number label is seen with maximum relaxation by the subject. This gives a measure of spherical power to ±0.25D.

To improve the accuracy of the measurement, +0.25D and −0.25D lenses could be placed in the path of the reference beam and another check made of the highest number label seen clearly by the patient. From these measurements the spherical refractive error of the patient can be decided to within ±0.125D. The range of numbers seen by the patient gives the accommodation range.

Figure 5:
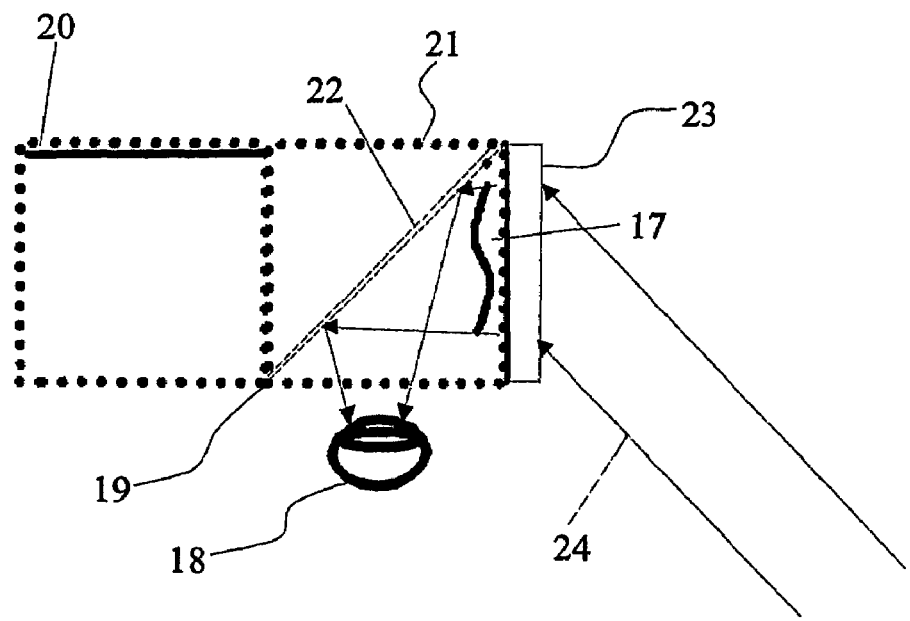
FIG. 5 shows a device for working the invention.
Figure 6:
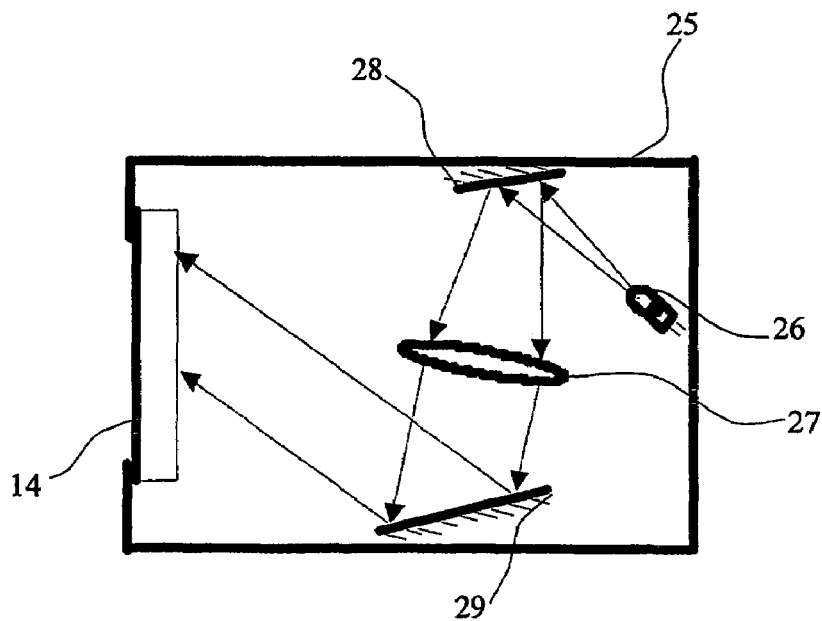
FIG. 6 shows an illumination system for the device of FIG. 5.

The invention can be put into practical effect using the arrangement shown in FIG. 5. A hollow rectangular case 19 is divided into an occluded compartment 20 and an active compartment 21. The case 19 is placed in front of the eyes of a patient. The active compartment 21 carries a beam splitter 22, as shown. A beam splitter will be transparent and therefore enables the subject to relax his/her vision in viewing a distant object/screen within the room until the hologram is activated, whereas a mirror would give the feeling of looking into an instrument and might trigger his/her accommodation (instrument myopia). A window 23 on a sidewall carries the hologram 14. The hologram is illuminated by a plane wave 24 from an illuminating system contained in an adjacent light box 25, as shown in FIG. 6. The illumination system consists of a laser diode 26, collimating lens 27, and beam steering mirrors 28, 29 that direct the plane wave 24 at the hologram 14 at the appropriate angle. In the arrangement of FIG. 5, the hologram is flipped to bring about a reversal in direction. The reconstructed wavefronts are deflected by the beam splitter 22 towards the patient's eye 18. The patient will therefore see the characters as if they were flashed in front of him.

The inventors speculate that the cylinder power and axis of the human eye can be estimated by the following method: The labels on the pegs in FIG. 1 are replaced by radial line patterns having about 10° angular spacing between the lines and a hologram of the same is recorded as in FIG. 2. This hologram is then used in the device shown in FIG. 5. The subject viewing the hologram identifies the two indicia for which sharpest lines are seen. The line oriented along the cylinder axis would appear sharpest at one extreme end of the subject's accommodation range and the line perpendicular to the cylinder axis would appear sharpest at the other extreme end of the subject's accommodation range. From the subject's response an estimate of the cylinder axis can be obtained to within 10° in the positive or negative cylinder format. The difference between the spherical accommodation range while viewing the number labels and the accommodation range while viewing the radial lines would give a measure of the magnitude of the cylinder power. The number of neighbouring lines that appear fairly sharp (without blur) while viewing the sharpest line along the axis or perpendicular to the axis at the two extreme ends of the accommodation range would also indicate the magnitude of the cylinder power. The method offers the unique advantage of simultaneously presenting radial patterns at various vergences to the subject.

The case of FIG. 5 can be modified to measure both eyes simultaneously by reproducing the components in the active compartment 21. Activating the compartments alternately the practitioner will be able to conduct binocular refraction. In binocular refraction the subject is allowed to keep both the eyes open while the target is shown only to one eye at a time. To achieve spherical balancing binocularly both the eyes are corrected until the subject sees the character '0' clearly and comfortably with each eye. Binocular spherical balancing provides comfortable vision as it ensures stability of accommodation between the eyes.

Figure 7:
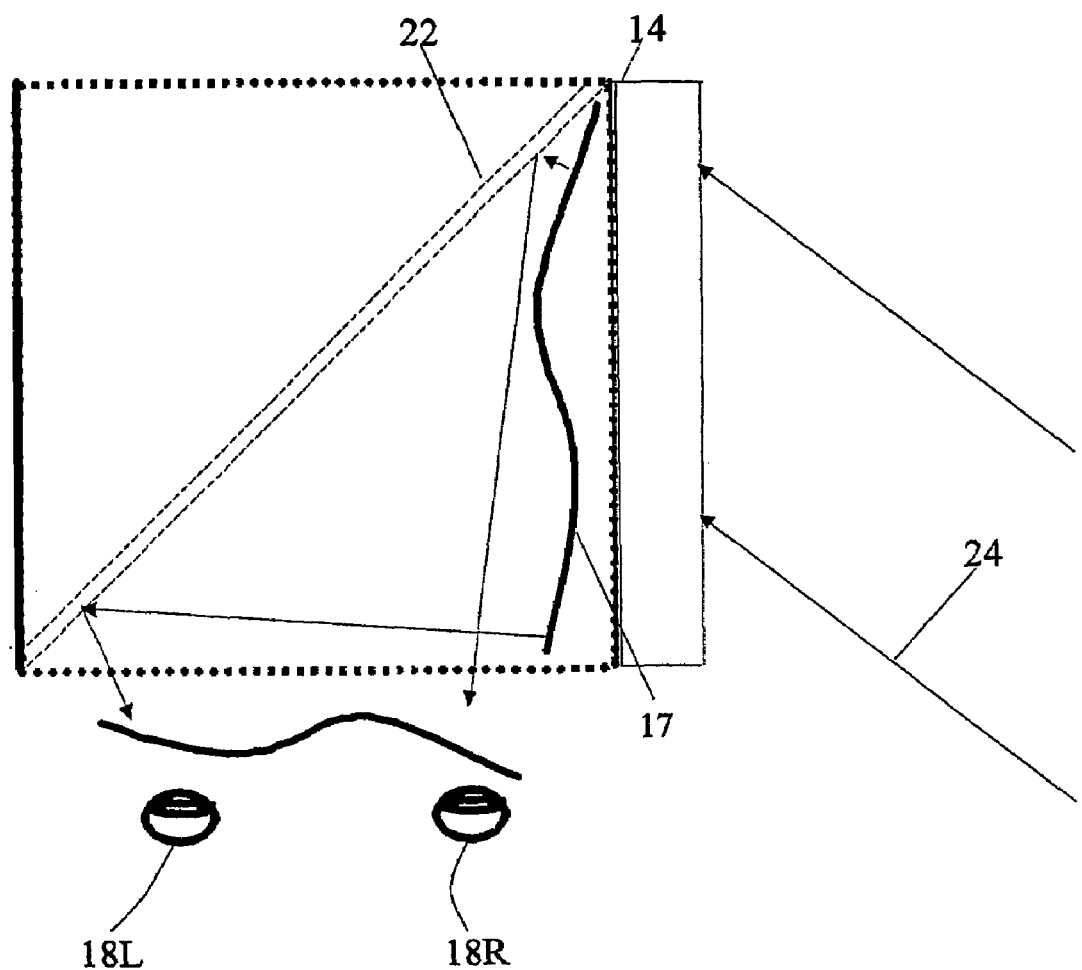
FIG. 7 shows a device for testing stereopsis.

A variation of the invention can be used to diagnose stereopsis problems. With reference to FIG. 7, to test for stereopsis the invention is scaled to produce a large hologram, large enough for both the eyes (18L, 18R) to receive the reconstructed wavefront from the object scene simultaneously. To record such a hologram a large coherence length laser and a large focal length lens in place of the 20D lens would be used in the setup of FIG. 2. The 3D object would be suitably redesigned for stereopsis measurements. Use of such a hologram would be superior to the stereograms currently in use. Stereograms that are currently in use simulate 3D scenes with the limitation of having a single percept of the object scene. Whereas the holograms would reconstruct a truly 3D wavefront of the object scene. The depth perception of the subject would simply be ascertained by the subject indicating which elements are seen to be closest and which furtherest away. The location of the eyes, the interpupillary distance and the convergence of the eyes will not affect the performance of the hologram.

Throughout the specification the aim has been to describe the preferred embodiments of the invention without limiting the invention to any one embodiment or specific collection of features.

The disclosures of each and every patent, patent application, and publication cited herein are hereby incorporated herein by reference in their entirety.

The invention claimed is:

1. A device for measuring spherical refractive error of the human eye of a subject comprising:
   a holographic element recording an image wavefront of a three dimensional array of indicia; and
   means for illuminating the holographic element with a plane wavefront of visible light such that when viewed the patient sees a reconstructed image of the array of indicia;
   wherein each indicia is seen at a different perceived distance from the subject.

2. The device of claim 1 wherein the array of indicia comprises a 4 by 4 array with labels ranging from −10 through zero to +5.

3. The device of claim 1 wherein the array of indicia comprises radial line patterns.

4. The device of claim 3 wherein the radial line patterns comprise an angular separation between adjacent lines of the radial pattern of about 10°.

5. The device of claim 1 in which the hologram is a large hologram that is viewable by both the eyes simultaneously to enable testing of stereopsis.

6. A method of measuring spherical refractive error of the human eye of a patient including the steps of:
   the subject viewing a reconstructed hologram of an array of elements with each element at a different perceived distance from the subject, and each said element bearing indicia; and
   the subject identifying one or more indicia that are seen to be in sharp focus.

7. The method of claim 6 further including the step of the subject identifying the range of indicia that are in focus to give a measure of amplitude of accommodation.

8. The method of claim 6 further including the step of presenting a hologram to each eye of a subject to facilitate spherical balancing binocularly.

9. A method of estimating cylinder power and axis of the human eye including the steps of:
   the subject viewing a reconstructed hologram of an array of elements, said elements bearing indicia in the form of radial line patterns; and
   identifying the radial lines seen as sharpest on the elements at the two ends of the accommodation range of the subject.

10. An apparatus for measuring characteristics of a human eye of a subject comprising:
    a case;
    an active compartment formed in one part of the case, said active compartment including a hologram recording a three dimensional array of indicia and a beam splitter directing a view of the subject at the hologram; and an adjacent light source directing collimated light at the hologram at an appropriate angle for reconstruction of the hologram;

wherein each indicia is seen at a different perceived distance from the subject.

11. The apparatus of claim 10 further comprising an occluded compartment in a further part of the case.

12. The apparatus of claim 10 configured for measuring binocular refraction further comprising a second active compartment including a hologram recording a three dimensional array of indicia and a beam splitter directing a view of the subject at the hologram; and means for selecting said first active compartment or said second active compartment for viewing by the subject.

13. A method of binocular balancing including the steps of directing a subject to alternately view said first active compartment and said second active compartment of the apparatus of claim 12 and inserting lenses into a viewing path of each eye until the subject obtains an equivalent view in each eye.

14. A method of diagnosing stereopsis problems in a subject including the steps of:

the subject viewing a large reconstructed hologram of an array of elements with both eyes, each said element being at a different perceived distance from the subject and each element bearing indicia; and the subject identifying which, if any, elements are perceived to be nearest and which are perceived to be furtherest from the subject.

15. A device for measuring spherical refractive error of the human eye of a subject comprising:

a holographic element recording an image wavefront of a three dimensional array of indicia; and means for illuminating the holographic element with a plane wavefront of visible light such that when viewed the patient sees a reconstructed image of the array of indicia;

wherein:

each indicia is seen at a different perceived distance from the subject; and the array of indicia comprises a 4 by 4 array with labels ranging from −10 through zero to +5; and the array of indicia comprises radial line patterns.

16. The device of claim 15, wherein the radial line patterns comprise an angular separation between adjacent lines of the radial pattern of about 10°.

* * * * *